United States Patent [19]

Pearce et al.

[11] Patent Number: 4,918,979
[45] Date of Patent: Apr. 24, 1990

[54] LIQUID TESTING APPARATUS

[75] Inventors: Derry F. Pearce, Airport West; Eugene Dimitriadis, Clayton; James R. Starkey, Mulgrave, all of Australia

[73] Assignee: Godfrey Howden Pty. Ltd., Australia

[21] Appl. No.: 200,161

[22] Filed: May 31, 1988

[30] Foreign Application Priority Data

May 29, 1987 [AU] Australia .................. PI2219/87

[51] Int. Cl.$^5$ ............................. G01N 29/02
[52] U.S. Cl. ............................ 73/61.1 R; 73/118.1
[58] Field of Search .............. 73/61.1 R, 61 R, 597, 73/118.1; 250/343

[56] References Cited

U.S. PATENT DOCUMENTS 3,478,578 11/1969 Dukek et al. ............... 73/61.1 R

FOREIGN PATENT DOCUMENTS

| A233047 | 8/1987 | European Pat. Off. . |
| 62-25254 | 2/1987 | Japan . |
| 62-25255 | 2/1987 | Japan . |
| 62-25256 | 2/1987 | Japan . |
| 717633 | 2/1980 | U.S.S.R. . |
| 1239586 | 6/1986 | U.S.S.R. . |
| 1259158 | 9/1986 | U.S.S.R. . |
| 1514977 | 6/1978 | United Kingdom . |
| 1550073 | 8/1979 | United Kingdom . |
| 2089032 | 6/1982 | United Kingdom . |
| WO87/02770 | 5/1987 | World Int. Prop. O. . |

Primary Examiner—Jerry W. Myracle
Attorney, Agent, or Firm—Sughrue, Mion, Zinn, Mackpeak & Seas

[57] ABSTRACT

The liquid testing apparatus comprises a housing incorporating a device for measuring the refractive index and a device for measuring the sonic velocity of the liquid under test. The housing comprises a chamber into which a prism protrudes and approximately collimated light is transmitted through the prism. By measuring the amount of totally internally refracted light, the refractive index of the liquid in the chamber is determined. A further chamber is provided in the housing and a sonic pulse transducer is disposed at one end of the further chamber which also receives the reflected pulse from the other end of the further chamber. A temperature sensor is also provided. The apparatus provides one or more signals to display the quality of the liquid and/or to provide a control of the liquid flow or of a device using the liquid. The apparatus may form part of a container drain plug and incorporate a drain valve.

17 Claims, 16 Drawing Sheets

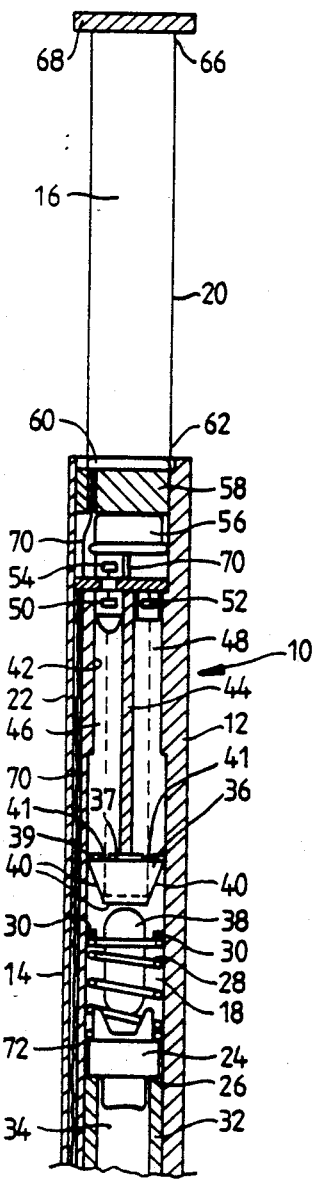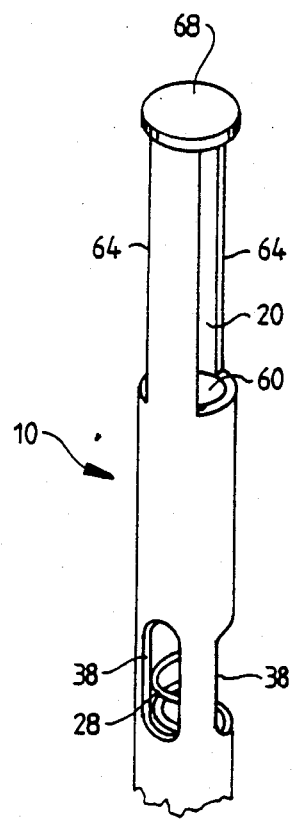
FIG 1
FIG 2

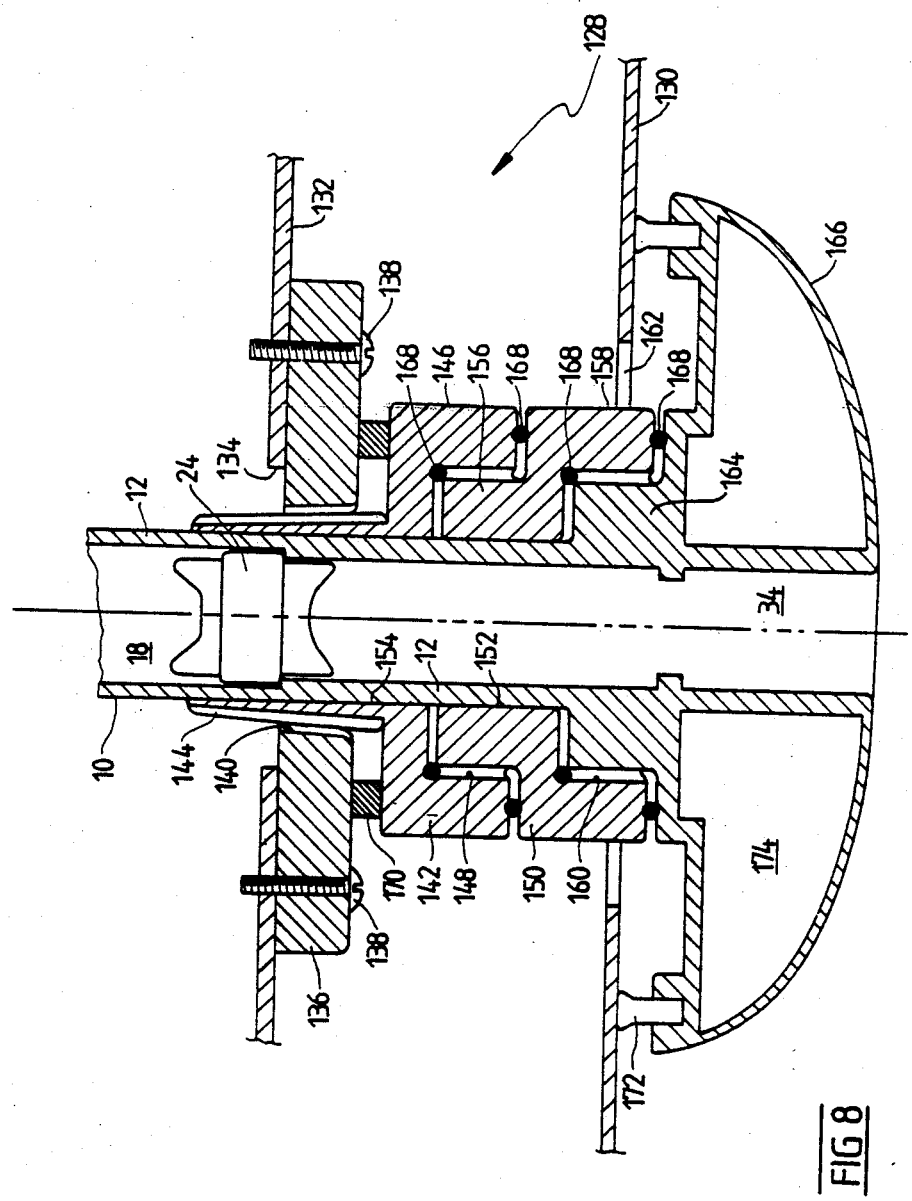

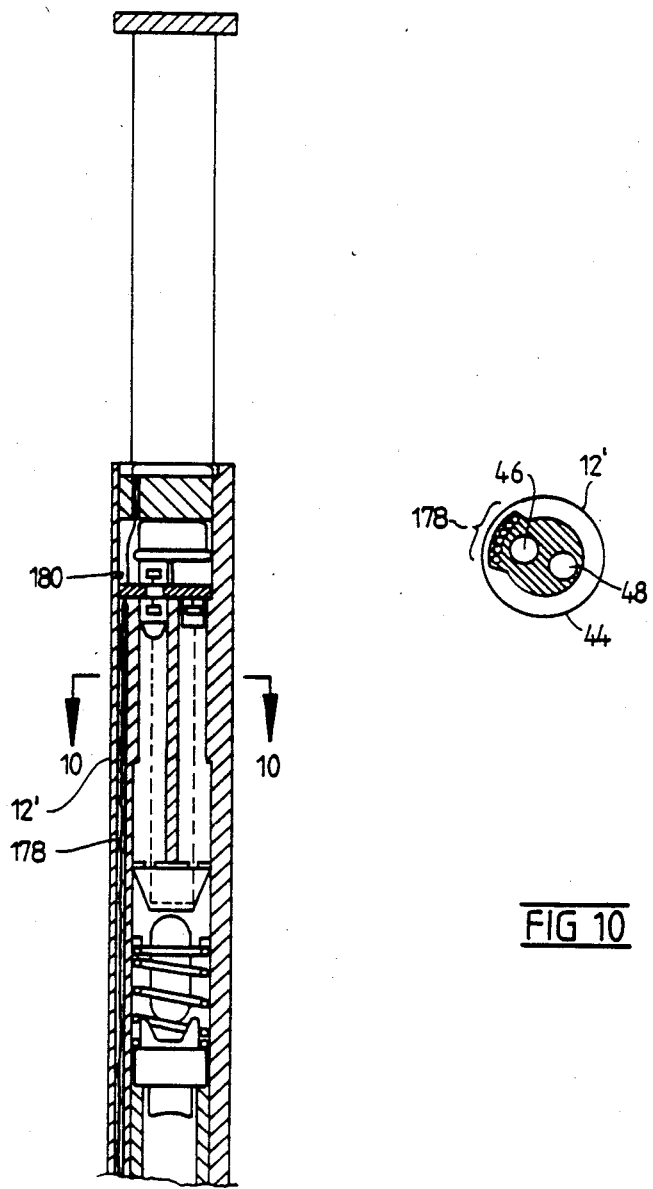

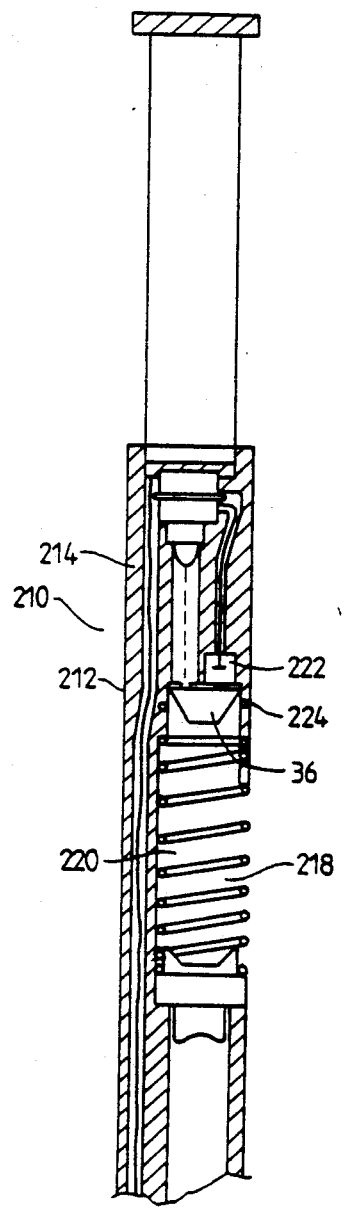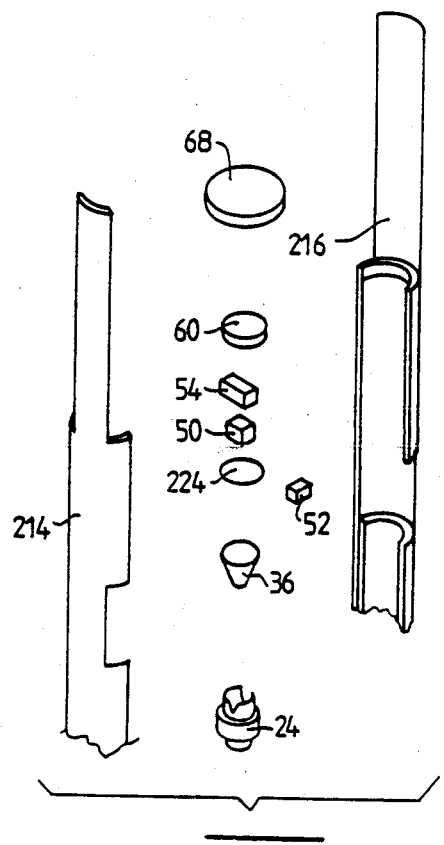
FIG 12a
FIG 12

LIQUID TESTING APPARATUS

The present invention relates to liquid testing apparatus and is particularly concerned with liquid quality monitoring. One non-limiting area of use of the present invention is in the need to ensure that the correct quality of fuel is to be supplied to aircraft and other engines and that no contaminating liquid such as water is present in the fuel. The present invention has particular advantage in determining the proportions of different fuels in a mixed fuel supply, such as methanol and unleaded petrol, for automobile and other vehicle engines.

The need to test the quality of aviation fuels has long been recognised and it is a general requirement of a pilot to perform suitable tests on fuel in each fuel tank prior to a flight and following a fuel tank refill. Commonly this is performed by removing a sample of the fuel from the tank and subjecting it to one or more of various subjective tests including smell and visual appearance. The visual test will generally identify the presence of water in the fuel which may lead to catastrophic engine failure or malfunction, and may identify differently colored fuels. However, such visual tests are commonly performed in conditions of bad light and are subject to human error.

Flexible fuelled vehicles, usually running on mixtures of alcohol and petrol, have been proposed in order to reduce pollution of the environment by exhaust gases emanating from the combustion of the fuel. Vehicle engines must be set to run at their optimum for a particular grade of fuel and if the quality of the fuel changes it is important to modify the engine setting in order to maintain performance. This may be done on an occasional basis but preferably the fuel is monitored on a substantially continuous basis in which case the engine settings may be controlled automatically according to the fuel quality, as well as other factors, by an engine management system.

It has previously been proposed to test the quality or presence of liquids, including fuels, objectively by measuring a particular parameter. One parameter on which work has been performed is refractive index.

In some instances, refractive index measurement can give reliable qualitative results but the testing of aircraft fuel must be performed over a very wide range of temperatures such as above 50° C. down to −40° C. due to the location of aircraft throughout the world. Refractive index is dependent on temperature and in order for a measurement device to satisfactorily cover this range of temperature variation it must be made very sophisticated and therefore expensive. It is possible to produce a simple refractive index measurement device but in order to obtain the desired sensitivity to discrminate or give an indication of discrimination between liquids or liquid and gas, it must be calibrated for a relatively narrow range of refractive indices. Outside this range, the discriminating ability drops off. Since the temperature variation and/or variation in the acceptable composition of the liquid being discriminated, as well as contamination in the liquid, may take the refractive index outside the prescribed range, refractive index measurement as a method of discriminating liquids may not be reliable. For the above reasons, refractive index determination has not been used to any great extent in aircraft fuel discrimination.

Additionally, and particularly in relation to flexible fuelled vehicles, the sensor measuring the refractive index of the fuel must be in contact with the fuel and may become contaminated by residue build-up from the fuel. This will tend to cause inequalities in the measured refractive indices which may not at least initially be readily identifiable.

It has also been proposed to analyse liquids by way of their density and there are many ways of ascertaining this parameter. One such method has been proposed in U.S. Pat. No. 4117716 in which the density of a fluid has been determined from its sonic velocity which is measured by ascertaining in voltage terms the amount of energy absorbed by the fluid. Sonic velocity might be proposed for discriminating liquids but in many cases the sonic velocities of different liquids are similar. Thus, in the case of aircraft fuels, the discrimination between many Avgas grades using sonic velocity is poor. In addition, it has been found that the sonic velocities of water/ice and many fuels are poorly discriminated at least over the range −5° C. to +5° C. Accordingly sonic velocity is not a satisfactory discrimination for many liquids and has not been found appropriate for discriminating mixed vehicle fuels or aircraft fuels and contaminants.

It is accordingly an object of the present invention to facilitate the testing of liquids, particularly but not essentially fuels. It will be understood that the present invention may be utilized in many areas other than fuels, including analysing liquid sugar concentrations, alcohol concentrations in fermented products, qualities of vegetable oils, adhesives, paints and solvents, surfactants and detergents and chemical and salinity concentrations as well as in the testing of medical and biomedical fluids.

According to the present invention, there is provided liquid testing apparatus comprising a housing defining at least one chamber capable of receiving liquid to be tested, optically transparent reflecting means in the housing and having a plurality of reflecting surfaces or a curved reflecting surface in said chamber or in one of the chambers, light transmitting means in the housing for radiating light onto said reflecting means, reflected light receiving means in the housing for receiving light from the transmitting means which has been reflected on said surface or surfaces and means for converting said reflected light into a first electrical signal indicative of the refractive index of the liquid, means in the housing for generating at least one sonic pulse and for transmitting same through liquid to be tested in said chamber or in a further one of the chambers, means in the housing for generating a second electrical signal indicative of the sonic velocity of the liquid and derived from said at least one transmitted pulse, and means for transmitting said first and second signals or at least one further signal derived from said first and second signals for determining the quality of the tested liquid.

By the present invention, the limitations of testing a liquid by means of sonic velocity assessment alone may be alleviated by also measuring the refractive index of the liquid. The refractive index measuring means may be relatively simple since it need primarily only be set up to discriminate a relatively narrow range of sensitivity where the measured sonic velocity may not be capable of discriminating. Further while the refractive index sensor may become fouled over a period of use by contact with the liquid under test, and thereby give rise to irregular readings, the sonic velocity sensor should not be so affected. At measuring points where there is overlap between the ranges of the sensors, a changed reading of the refractive index would indicate that the refractive index sensor is contaminated. The sensor may then be removed and cleaned.

It will be noted that refractive index and sonic velocity may not be unique characteristics of liquids to be tested which are mixtures, such as fuels, and consequently may not be absolute or inviable indicators of a particular liquid mixture. In practice, however, it is anticipated that the range of possible liquids that might be inadvertently or incorrectly substituted in situations in which the apparatus of the invention is used may be readily discriminated. Furthermore, where the components of the liquid mixture are known, as in the fuel for a flexible fuelled vehicle, the apparatus of the invention may provide a signal indicative of the proportions of the various liquids in the mixture.

A particular advantage of the present invention is that circuitry associated with refractive index and sonic velocity measurement may be relatively easily miniaturized so that the testing apparatus may be incorporated within small dimensions, and that only small volumes of liquid are required to complete the tests. In particular, the apparatus may be made sufficiently small as to readily be incorporated in an aircraft or other vehicle fuel tank since the provision of the sonic velocity sensor allows the reflected light converting means to be substantially simplified over previous proposals.

It will be noted that the liquid testing apparatus of the present invention does not rely on capacitance/dielectric constant measurements, so water absorption by liquids under test, particularly fuels does not cause problems for the apparatus and, indeed, can be distinguished. In liquid testing apparatus employing capacitance/dielectric constant measurements, water absorption can increase the conductivity of the liquid being tested to the extent that meaningful results cannot be obtained.

The signal or signals for determining the quality of the liquid under test which are provided during use of the apparatus may be used by an engine management system in a vehicle engine to control the running of the engine according to the quality of the fuel determined. In the case of a mixed fuel such as alcohol and petrol, the signal would preferably represent the proportion of alcohol to petrol. The engine management system may also be dependent on other measured signals such as air flow, engine temperature and so forth.

Alternatively the signal or signals for determining the quality of the liquid under test may be used to provide a display or visual indication of the quality of the liquid, such as by giving a read-out of the quality of the liquid or, for example, by illuminating a particular light according to the determined quality.

The liquid testing apparatus of the present invention may comprise an integral unit including display means to give an indication of the result of the testing and may, for example, be hand-held or form an integral part of a storage tank, flow line or other liquid containing device. In an embodiment in which the apparatus is not disposed on or in the liquid containing device the at least one chamber may comprise or form part of a container for holding the liquid into which a sample of the liquid to be tested is introduced. In an alternative arrangement in which the apparatus is fixed relative to the liquid storage or other container, the chamber or chambers may be open to the container for example by means of one or more slots in the side of the or each chamber.

Where the liquid testing apparatus is disposed in a flow-line of the liquid under test, it is preferably mounted in the top wall of the flow-line, particularly an enlarged portion of the flow-line, so as to be readily accessible without having to drain the flow-line.

In another embodiment there is provided a liquid container drain plug comprising a plug body capable of co-operating with an opening in the container to seal the opening, said plug body defining at least one chamber having an opening thereto whereby in use liquid in the container is capable of entering the chamber, liquid testing means disposed in the body to determine one or more preselected physical parameters of liquid in the at least one chamber, and means to generate at least one electrical signal indicative of said parameter or parameters for display. Conveniently, but not necessarily, the liquid testing means may take the form of the liquid testing apparatus of the present invention.

By this embodiment, testing of liquids may be facilitated by the simple expedient of replacing a standard drain plug in a liquid container such as a fuel tank with the defined drain plug. Advantageously, the drain plug has a closable outlet for permitting controlled exhaustion of liquid in the container therethrough.

The drain plug may be connected directly with means, such as a display or an engine management system, using the signal or signal determining the quality of the liquid. Thus, the drain plug may include display means for giving an indication of the quality of the liquid tested, but in a preferred embodiment such display means is remote from the drain plug and may, for example, be provided in a hand-held interrogator.

For convenience, the present invention will now be described generally with reference to testing fuel in an aircraft fuel tank, but it will be understood that the apparatus and drain plug of the invention may be used in many other situations and that the following description may be applied to, for example, testing the fuel in a flexible fuelled vehicle.

The testing apparatus of the present invention may be essentially permanently actuated so as to give the possibility of a continuous display or measurement of the parameter or parameters being tested in the liquid. Where a remote display means is provided, this may be such as to merely receive a signal from the testing apparatus which causes a read-out in the display means to give an indication of the parameter(s). However, an arrangement which was a continuous measurement may use a considerable amount of power in the testing apparatus during periods when the measurement is not in fact required and it is preferred that the testing apparatus provides intermittent testing of the or each parameter. Such intermittent testing may be initiated by an appropriate actuating signal which when received by the testing apparatus actuates the testing apparatus to perform the test or tests and display the information or transmit the information for remote display or for remote use of the signal or signals.

A remote display may be electrically connected to the testing apparatus but most conveniently is cordless in which case the signals transmitted between the display means and the testing apparatus, including any actuating signal, may be infra-red. Alternatively, an actuating signal from the remote display means may be white light and could be provided, for example, from a high speed electronic flash of the type used with cameras. A camera-type flash may provide a maximum practical actuating signal power energy density to minimise the detection and power consumption requirements of the testing apparatus circuitry and is capable of providing a sufficiently intense and relatively unique signal as to render false interrogations improbable. Infra-red flash energy alone might be utilized to advantage, for example to maximise reponsivity of the detector, to minimize possible spurious response from other light sources such as flashing wing tip navigation lights and to alleviate the possibility of a residual image temporarily impairing the vision of the person requesting the display, but it is believed that generally a white light actuating signal will be appropriate.

Particularly, where a plurality of aircraft wing tanks are disposed close together and each is provided with non-continuous testing apparatus in accordance with the invention, it may be desirable that only one or selected ones of the testing apparatus perform the tests when actuated. This may be arranged by sending coded signals to the plurality of testing apparatus with only one or the selected ones testing reacting to a particular coded signal, or by otherwise encoding the testing apparatus.

In one preferred embodiment, upon receipt of an actuating signal such as the high speed electronic flash, a more sensitive infra-red photo detector circuit may be activated which would only continue to maintain power to the testing apparatus following receipt of a set coding sequence. Such a coding sequence can be set by suitable means, for example miniature switches in the testing apparatus or programmed via a remote interrogator and/or display unit in a code setting or programming mode, into resident electrically alterable programmable read only memory (EAPROM) facilities within the testing apparatus.

Conveniently, in such an arrangement, the actuating signal detector means in the testing apparatus may be configured to actuate a testing apparatus battery switch which may be of MOSFET technology and which may itself be entirely passive. A fast response time photovoltaic photodiode or other detector may be employed to provide sufficient energy to directly turn on the gate of a MOSFET device and subsequently latch on the battery switch for an adequate time to complete the aforementioned interrogation decoding and, if appropriate, to complete the tests performed on the liquid.

If such testing apparatus identifies a received coded sequence from a remote display unit matching its internally set or programmed response code, it may commence its testing procedures on the liquid and display the resulting information, for example by transmitting it back to the read out unit or remote interrogator via an infra-red light emitting diode or similar means. If the received coded sequence did not match the set response code of the testing apparatus, the testing apparatus simply may go back to the inactive mode and conserve battery power without commencing a testing cycle. Advantageously, data transmission may be concurrent with data measurement in order to minimise random access memory requirements of the testing apparatus.

Utilizing a microprocessor, micro-controller or possibly a state machine implementation, the necessary measurement and comparison decision making processes may be readily programmed or hard wired into a remote display unit or directly into the testing apparatus, for example in a pod associated with the aforementioned drain plug. The display may be as direct values of the parameters tested or as a displaceable marker in a graded dial, but in many instances it will be satisfactory to merely have a signal identifying that the tested parameter falls within a required range and this may be provided by a variety of coloured lights. The size and power consumption of the testing apparatus may be minimized by locating the data processing electronics in a remote unit such as the remote display unit.

The refractive index measurement by the testing apparatus in accordance with the present invention may be performed by providing a suitably chosen refractive index transparent glass or other material (e.g. plastics) which is resistant to the liquid to be tested with a plurality of reflecting surfaces, such as a prism having three reflecting facets. The prism is immersed in the liquid so that the reflecting facets are sufficiently covered by the liquid to be tested and light, preferably essentially mono-chromatic and approximately collimated, is directed by a photodiode or other light transmitting means into a preselected part of the prism. The light transmitting means is preferably spaced from the prism and at least partial collimation improves the sensitivity of the device and optimises the useful refractive index range of the sensor. Collimation or directional control of the beam from the light transmitting means may be achieved in a variety of ways, for example by the use of lenses, straight light channels and narrow light guides such as optical fibres. Preferably the light is partly collimated by an opaque surface coating or film on the receiving surface of the prism, the coating or film having an appropriately positioned pin-hole to pass a narrow beam of light. The light beam, or part of it, will be transmitted from the prism, after internal reflections, to a receiving photodiode or other photodetector.

Given the optical path configuration, the refractive index of the prism material and the facet angles, then at a particular angle of incidence (corresponding to the critical angle for total internal reflection from Snell's Law) the beam will be totally internally reflected around the path defined by the prism and only attenuated by the absorption and scattering co-efficient of the prism material for a particular liquid refractive index. When the refractive index of the liquid contacting the prism facets is such that the angle of incidence of the beam in the prism is no longer greater than the critical angle between the prism material and the liquid, the beam will be at least partly refracted out into the liquid and the refracted light steeply attenuated as sensed by the light detector. Since the light beam will not normally be perfectly collimated and will have finite area dimensions (as does the entrance pupil of the light receiving detector) the steepness of sensitivity of the attenuation curve can be adjusted as a function of the refractive index of the liquid. In this way, the refractive index measurement system components and configuration can be optimised for any preselected range of refractive index measurements.

The refractive index measurement means may be increased in sensitivity by varying the number of facets in the prism. In one embodiment, the prism may be configured as a continuous light transmitting bent rod or filament disposed in the liquid so that the light beam directed into an input end is reflected from the walls of the rod or filament around to a receiving end. Furthermore, the colour of the beam may be adjusted within available facilities to ensure that the prism and liquid refractive indices are best suited to the attainable sensitivity range or other factors.

Advantageously the portion of the optically transparent means in contact with the liquid may be coated to resist wetting by water. A suitable coating may be of reactive silicone material, including silanes of various types.

Sonic velocity may be measured in the testing apparatus of the present invention by determining the time of flight of a sonic wave or pulse in the test liquid. The sonic velocity measurement may be performed in the same chamber of the testing apparatus as the refractive index measurement or in a separate chamber. A pulse or number of pulses may be generated at the face of a piezo-electric cell or other transducer at one end of the chamber so that the pulse or pulses travel outwards into the test liquid to be received by another transducer at the other end of the chamber, or by the same transducer if the pulse is reflected back from a suitable reflector in the test chamber. Generally, only part of the pulse transmitted energy impinges onto the receiving transducer and is converted back into electrical energy. This can be amplified and timed accurately in relation to the period of transmission. Other means of measuring sonic velocity, such as phase-shift measurements made with standing waves (eg. sinusoidal) formed with appropriate excitation or as described in U.S. Pat. No. 4117716 may be used, but time of flight sonic velocity is believed to offer optimum ease of fabrication and manufacturing costs in the preferred embodiment.

The time of flight sonic velocity measurement can be optimised by various factors. The transducers can be improved in energy conversion efficiency and pulse response by appropriate material selection, electronic impedance matching and using transducer coating materials as acoustic matching layers and coupling means. The diameter and other basic dimensions as well as surface topology of the radiation transmitting and receiving face or faces and/or the reflecting face can be selected to yield a suitably directive radiation pattern to minimise spurious reflection responses and pulse dispersion. Spurious reflections may also be reduced by surface treatment of the test chamber. In a preferred embodiment a simple cylindrical tube with slotted walls to admit the liquid proved adequate. The transmitted and/or received pulse shape may be tailored and optimised simply by appropriate choice of electronic and mechanical damping means to minimise timing ambiguities due to ringing. If so desired, accuracy of sonic velocity measurement may be improved by averaging the measured periods of a plurality of pulse transmissions. Further, improved pulse detection may be provided by use of a separate pulse receiver which makes it unnecessary to have a reflecting surface. However, the reflecting configuration allows a shorter test chamber to be used.

Refractive index and sonic velocity are both subject to temperature variation and the measurements may be performed at a preselected temperature for which the apparatus has been set up. Alternatively, means may be included in the testing apparatus to measure temperature and to display or transmit an appropriate signal or, preferably, to compensate for variation from a norm in the refractive index and sonic velocity signals. However, such compensation may not be able to improve discrimination between liquids outside the preferred range of measured refractive indices.

In one embodiment, the sonic velocity and refractive index measuring means are disposed in a cylindrical housing which may form part of the aforementioned drain plug. Conveniently, particularly where space is at a premium as in a drain plug, the sonic velocity and refractive index measurements are performed in separate chambers at or adjacent respective ends of the cylindrical housing and slots are provided in the wall of the housing to permit access of the liquid under test. The measuring means, for example including a prism, a temperature transducer and a sonic pulse transmitting transducer, are conveniently disposed in a sealed portion of the housing between the chambers. The chamber in which the refractive index prism is disposed may have a closable drain valve at the opposite end. The cylindrical housing may be connected with a pod containing electronic circuitry for receiving signals from the measuring means, interpreting and displaying them and/or transmitting them to a remote display unit which conveniently also interprets the signals. The pod is conveniently external of the liquid container. Alternatively, the signal or signals may be transmitted by the circuitry to additional receiving means such as a control device, for example an engine management system.

In another embodiment, the measuring may be performed in the same chamber with a frame or slotted structure being disposed within the common chamber to substantially contain the sonic pulse or pulses. Such an arrangement is most preferred where the chamber is separate from the container of the liquid under test and receives a sample from the container, or where space is not at a premium.

Various embodiments of testing apparatus in accordance with the present invention will now be described by way of example only with reference to the accompanying drawings in which:

FIG. 1 is a sectional elevation of a first embodiment of the testing apparatus;

FIG. 2 is a reduced perspective view of part of the apparatus of FIG. 1,

Figure 3:
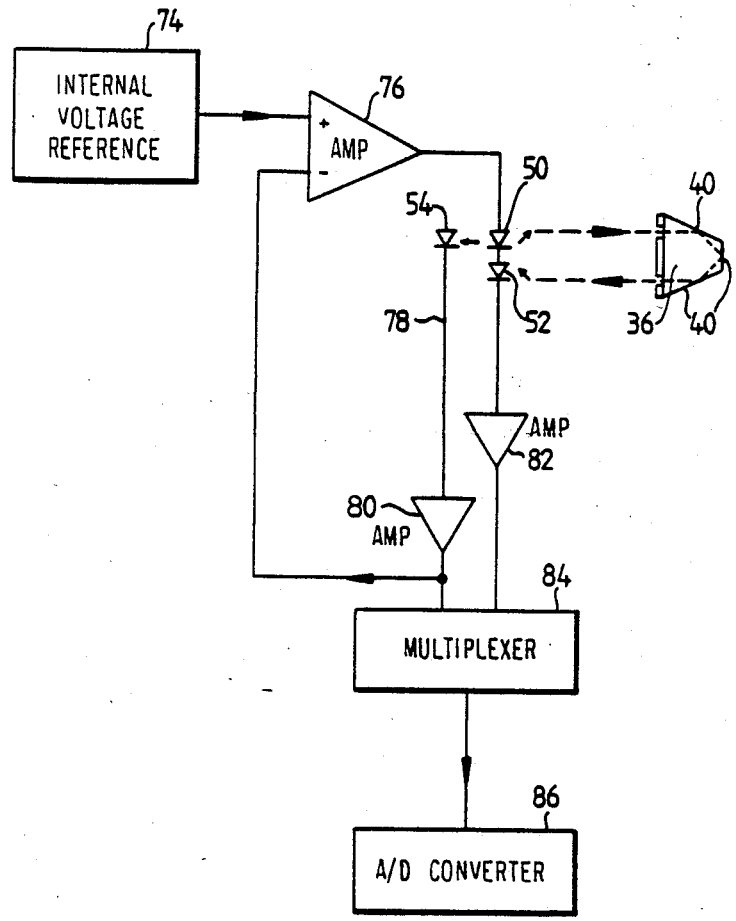
Figure 4:
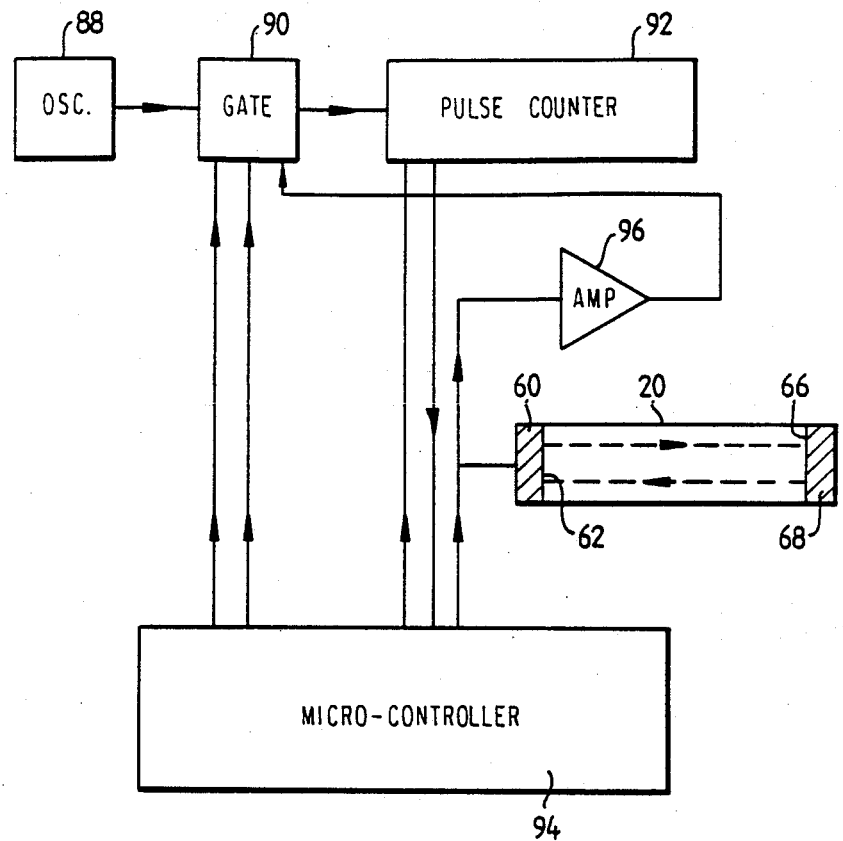
Figure 5:
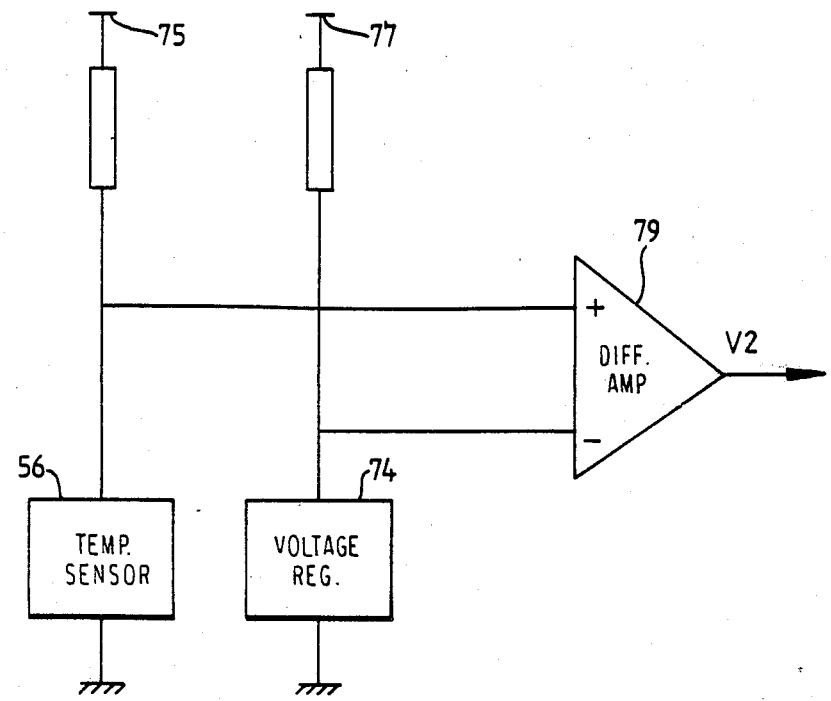
Figure 6:
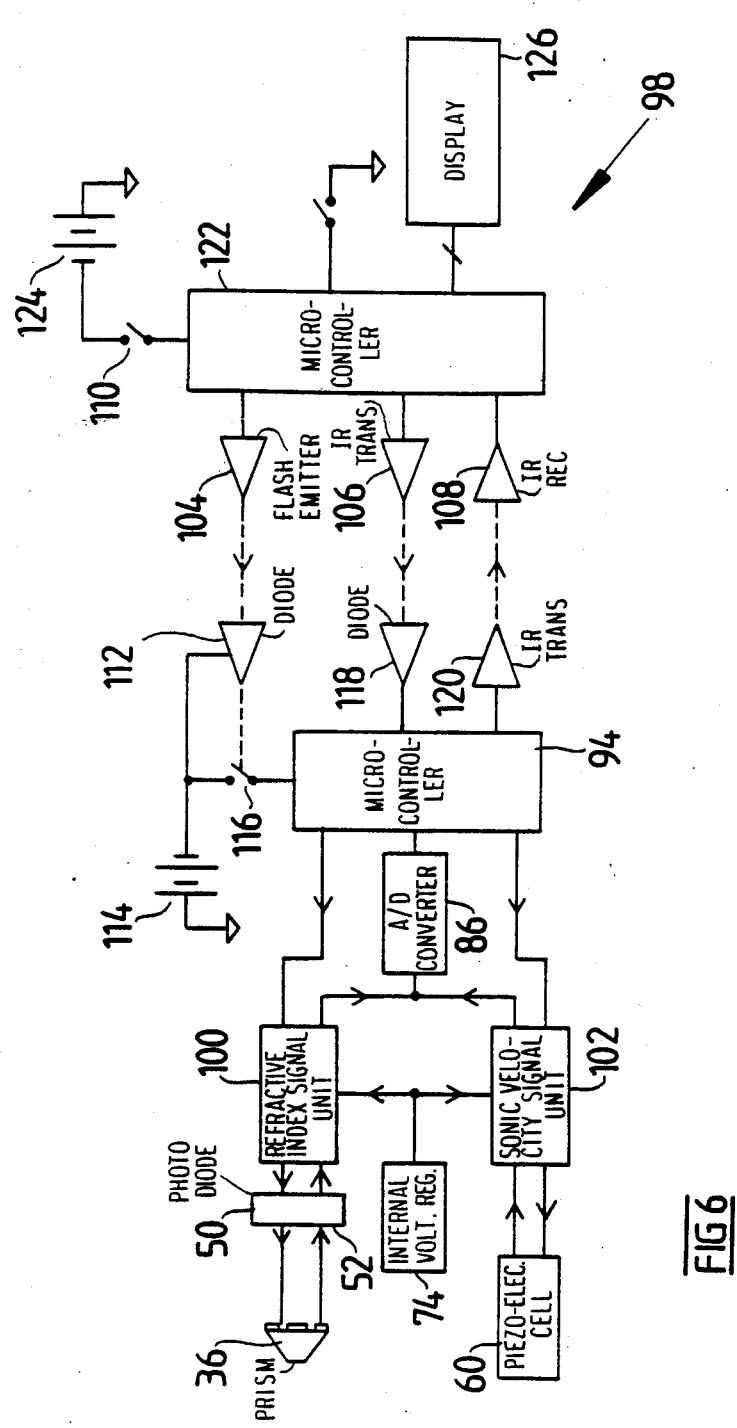
Figure 7:
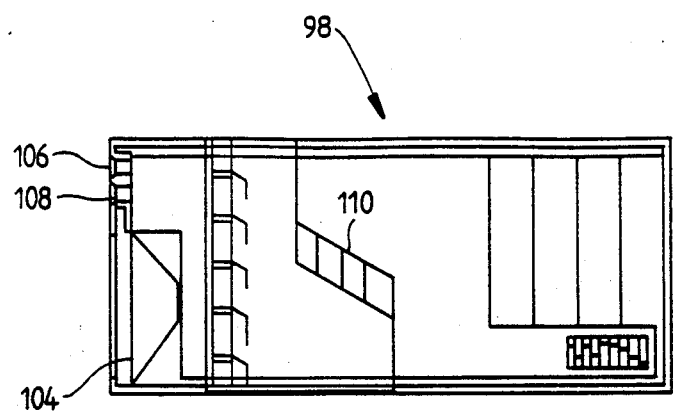

FIG. 3 is a schematic circuit diagram of the refractive index measurement performed by the testing apparatus, FIG. 4 is a schematic circuit diagram of the sonic velocity measurement performed by the testing apparatus, FIG. 5 is a schematic circuit diagram of the temperature measurement performed by the testing apparatus, FIG. 6 is an overall schematic circuit diagram of the testing apparatus and of a remote interrogator and display unit, FIG. 7 is a plan view of a remote interrogator and display unit, FIG. 8 is a sectional elevation of one embodiment of drain plug incorporating a pod to receive the electronics of the testing apparatus, the testing apparatus being omitted for convenience, FIG. 9 is a view similar to FIG. 1 but showing a second embodiment of the testing apparatus, FIG. 10 is a cross-sectional view taken on the line 10—10 of FIG. 9.

Figure 11:
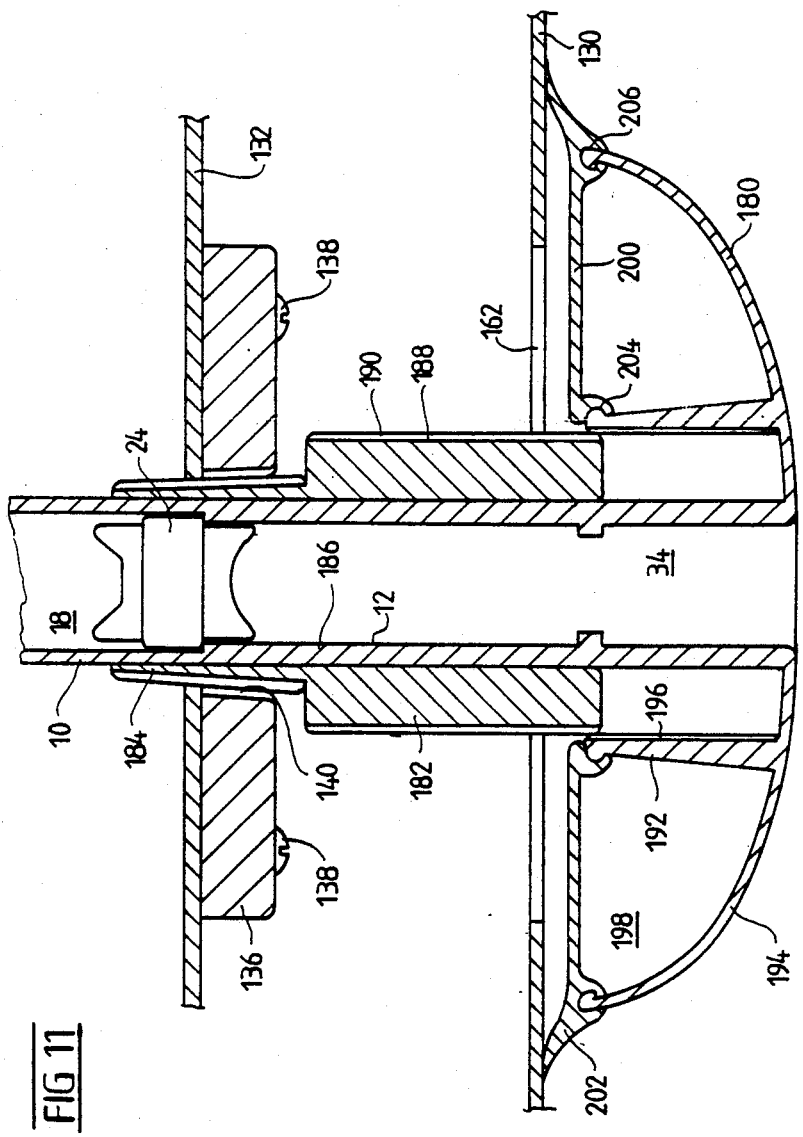
Figure 13:
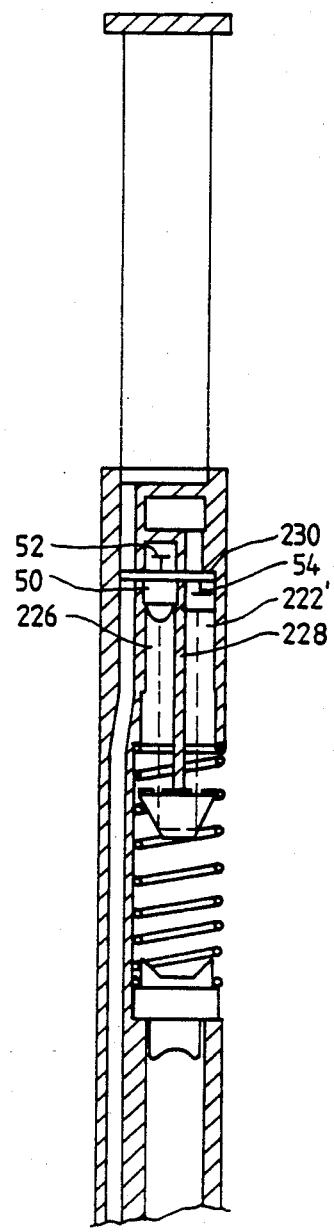
Figure 14:
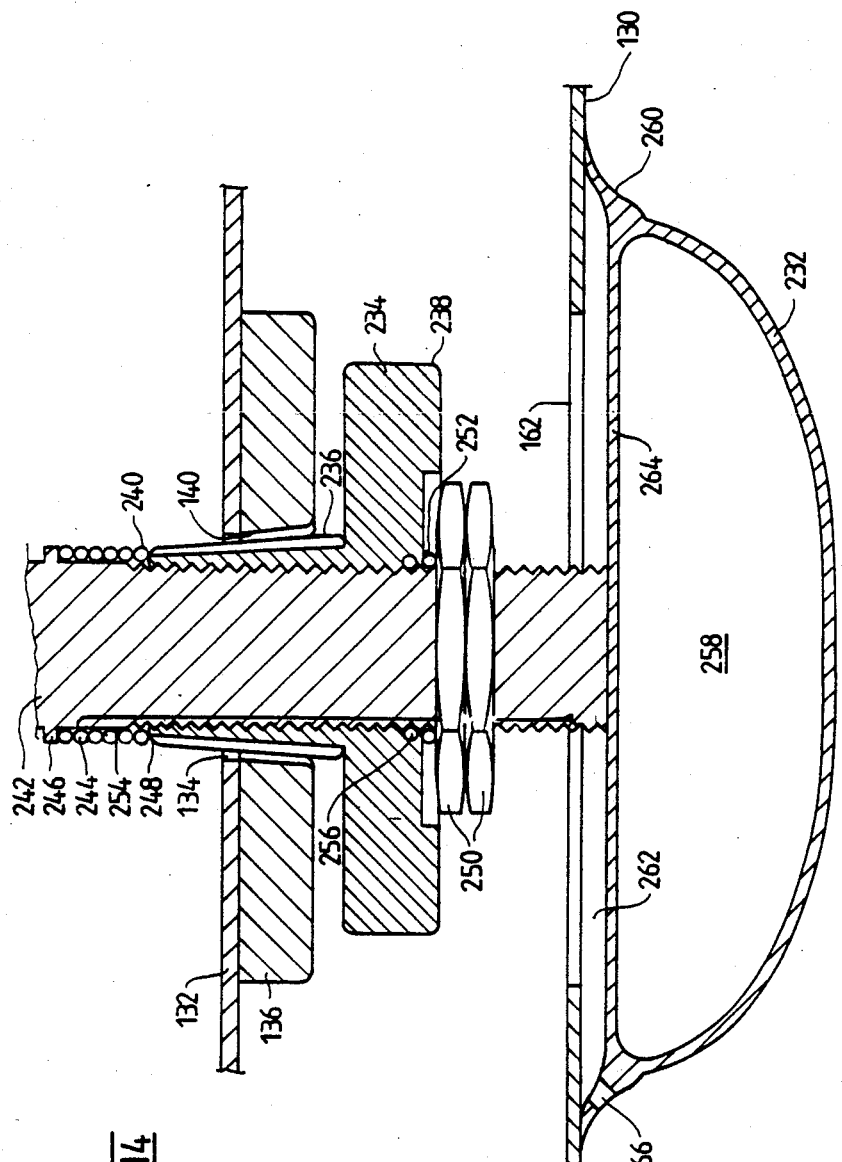
Figure 15:
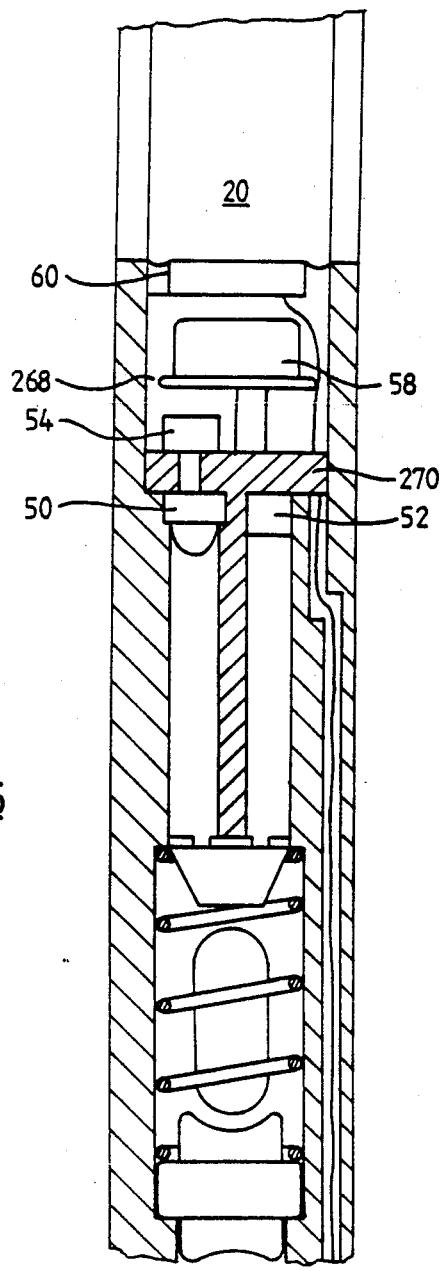
Figure 16:
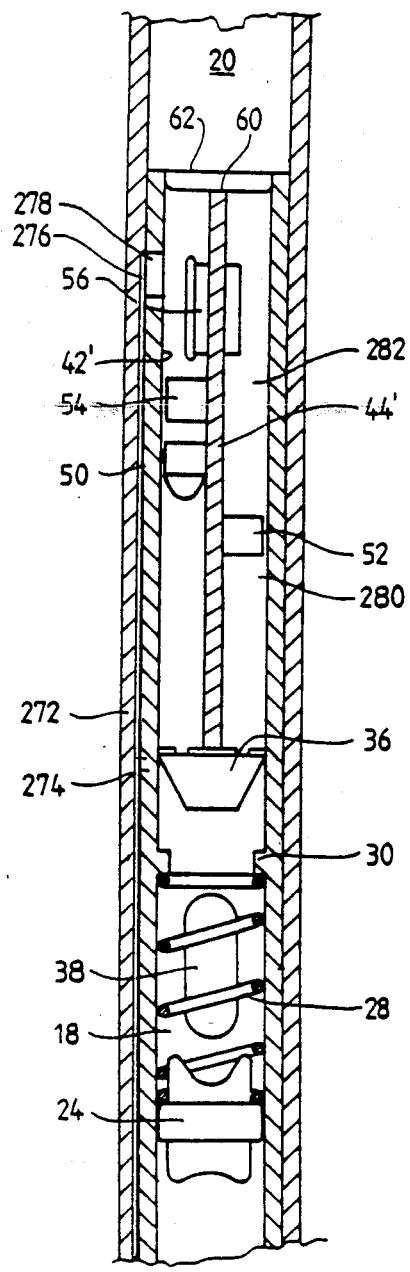
Figure 17:
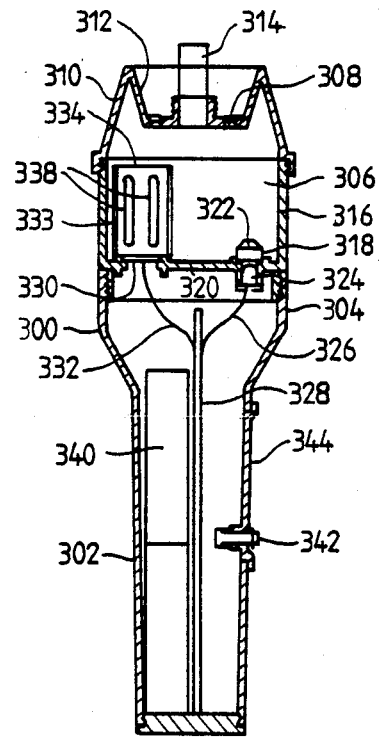
Figure 18:
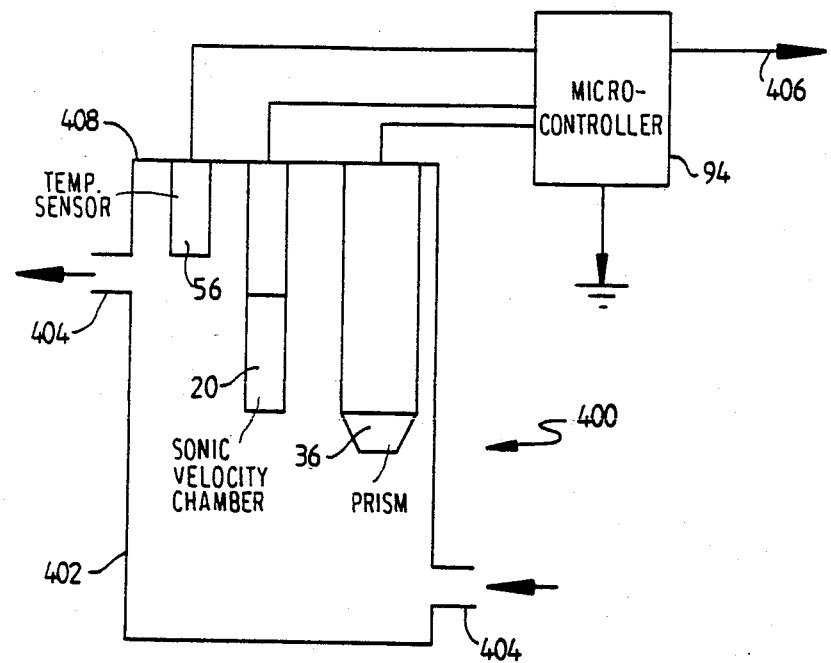

FIG. 11 is a view similar to FIG. 8 but showing a second embodiment of the drain plug and electronics pod, FIG. 12 is a view similar to FIG. 1 but showing part of a third embodiment of the testing apparatus, FIG. 12a is a reduced exploded view of the third embodiment of testing apparatus, FIG. 13 is a view similar to FIG. 12 but showing a fourth embodiment of the testing apparatus, FIG. 14 is a view similar to FIG. 8 but showing a third embodiment of the drain plug, FIG. 15 is a partial view similar to FIG. 1 but of a further embodiment of testing apparatus, FIG. 16 is a view similar to FIG. 15 but of a still further embodiment of the testing apparatus, FIG. 17 is a schematic sectional view of a hand held testing apparatus, and FIG. 18 is a schematic view of the testing apparatus modified for use in a fuel line.

The following description of apparatus in accordance with the invention as embodied in FIGS. 1 to 17 will be given primarily with reference to apparatus located in a fuel tank in the wing of an aircraft and incorporating a drain valve. However, as has been indicated above the testing apparatus of the invention may be used in many other locations and the description is not to be construed as limiting in this respect. Furthermore, it will be will be understood that the drain valve is not an essential feature of the apparatus of the present invention.

The testing apparatus 10 shown in FIGS. 1 and 2 comprises a housing 12 having opposed end portions 14 and 16 respectively defining chambers 18 and 20 which are open to atmosphere and a central portion 22 which is sealed from atmosphere.

The housing 12 is of elongate tubular configuration and the components of the testing apparatus described below close off the central portion 22. One end of the chamber 18 is closed off by a drain valve 24, preferably formed of plastics material, which is biased into a closed position on a valve seat 26 as shown by a compression spring 28 which bears against projections 30 in the first chamber. The valve seat 26 is formed on a tubular shoulder portion 32 within the housing 12 and the drain valve 24 may be opened by inserting a projection through the passage 34 defined by the shoulder portion 32 to bear against the drain valve 24 and compress the spring 28.

The other end of the first chamber 18 is closed off by one end of a relatively short prism 36 and the first chamber is open to atmosphere, or in use to the testing liquid, by way of opposed slots 38 in the wall of the housing.

The prism 36 is formed of glass of appropriate refractive index and has three facets 40 at the said one end in the chamber 18. Said end may be coated with a silane to resist wetting of the prism by water. The other end 37 of the prism is open to a chamber 42 within the central portion 22 of the housing which is divided longitudinally by a wall 44 to define outgoing and return light paths 46 and 48 respectively for light directed along the light path 46 onto said other end of the prism and returned along the light path 48 following reflection on the facets 40. Briefly, monochromatic light is emitted by a photodiode 50 along the outgoing light path 46 onto the other end 37 of the prism 36. The other end 37 of the prism has an opaque surface coating 39 thereon of any appropriate material, the opaque coating 39 having a pin-hole opening 41 therethrough in each of the outgoing and return light paths 46 and 48 so as to approximately collimate the emitted and reflected light. Light reflected by the facets 40 into the return light path 48 is picked up by a receiving photodiode 52 and the received light is compared with the emitted light in order to determine the refractive index of the liquid in which the facets 40 of the prism are immersed in the chamber 18. The light emitted by the diode 50 is monitored and appropriately controlled by a monitoring photodiode 54.

Refractive index and sonic velocity are subject to temperature, and a temperature sensor 56 is supported in the chamber 42 at the end remote from the prism 36. Said end of the chamber 42 is sealed by a plug 58 bonded to the walls of the housing 12.

On the side of the plug 58 remote from the temperature sensor 56 is disposed a piezo-electric cell 60 which has a sonic pulse transmitting face 62 disposed at one end of the second chamber 20. The chamber 20 is open to atmosphere, or to the liquid being tested in use, by means of slots 64 in the wall of the housing portion 16 which extend the length of the chamber 20. Thus, liquid under test is in contact with the pulse transmitting face 62 and a pulse from the cell 60 is transmitted through the liquid in the chamber 20. At the other end of the chamber 20 the pulse, or a series of pulses, is reflected by a reflecting surface 66 on an end cap 68 of the housing and the reflected pulse is received by the piezo-electric cell 60. Simply, the time of flight of the pulse or series of pulses is dependent upon the density of the liquid under test and the sonic velocity is determined by the delay between transmitting and receiving the pulse or series of pulses. Again, the sonic velocity is dependent upon temperature and the time of flight measurement may be adjusted for temperature variation.

The lower end (in the drawings) of the housing 12 is not shown and may comprise a handle or fixed pod containing appropriate circuitry to process the signals provided by the refractive index, sonic velocity and temperature sensing means. These means may be connected to the circuitry by, for example, ribbon cable or a flexible printed circuit board as shown schematically at 70 which passes through a channel 72 in the housing. Thus, the sensor 10 can measure refractive index and sonic velocity simultaneously and may share common electronic data processing and communication or display means. In addition, the sensor can be implemented simply and at low cost. Advantageously, the housing 12 can have a diameter as small as 8 mm.

Where the sensor housing 12 forms part of a handheld instrument or part of any other instrument which receives a sample of the liquid under test from a main tank, the drain valve 24 may not be required in which case the one end of the chamber 18 may be sealed by a plug similar to the plug 58. After testing, liquid in the chamber 18 may be exhausted through the slots 38.

Referring now to FIG. 3, a schematic representation of an electronic configuration for measuring refractive index in the apparatus 10 is shown, including the prism 36 and the photodiodes 50, 52 and 54. The light emitted by the diode 50 is stabilised against an internal voltage reference 74 of 2.50 Volts via a differential amplifier 76. The internal voltage reference 74 is also associated with the temperature measurement and sonic velocity measurement as described hereinafter.

Part of the light emitted from the diode 50 is directed towards the reference diode 54 which is matched, or at least very similar in characteristics to the receiving diode 52. The light transmitted to the reference diode 54 by the emitter 50 is ideally identical in output amplitude to the light directed by the emitter 50 into the prism 36. The output 78 from the reference diode 54 is fed to an amplifier 80 and to the differential amplifier 76 to provide a control of the light emitted by diode 50.

The signal created by the receiving diode 52 when the approximately collimated, reflected light beam impinges thereon is amplified in amplifier 82 and both the amplified receiving signal and the amplified reference signal are fed to a multiplexer 84. Advantageously the amplifiers 80 and 82 are also matched to minimize errors. From the multiplexer 84, a signal is transmitted to an analog to digital converter 86 allowing direct comparison measurements between the light beam emitted by the diode 50 and the beam received by the diode 52. In this way, quantitative measurements can be made of the refractive index of test liquids which have refractive indices within the desired measurement and resolution range of the optical measurement system.

Referring to FIG. 4 a preferred system for measuring the sonic velocity is shown, including the chamber 20, piezo-electric cell 60 and the end cap 68 with reflecting surface 66. An 8 MHz oscillator 88 is gated at 90 for one or a small number of cycles into the cell 60 to generate a sonic pulse or series of pulses at the surface 62 which passes through the test liquid in the chamber 20. Advantageously, the sonic pulse is generated with little received ringing in the test liquid by means of an appropriate acoustic matching layer such as an organic polymer on the surface 62 and with a correct selection of the number of half cycles input from the oscillator gate 90. Simultaneously, gate 90 is opened to allow an 8-bit pulse counter 92 to count cycles from the oscillator 88. The occurrence of the pulse burst is set by a micro-controller 94 which as shown in FIG. 6 is also associated with the temperature and refractive index measurement systems. The pulse is reflected by the surface 66 and the main reflection is picked up by the cell 60. The cell 60 emits a signal to an amplifier 96 so that the signal is amplified and turns off the gate 90. At this time, the number of pulses counted by the counter 92 is representative of the time of flight of the sonic pulse transmitted from the cell 60 and reflected back from the reflector surface 66 to the cell. The amplifier 96 conveniently has an input from the voltage reference 74 as shown in FIG. 6 and only transmits voltage signals above a predetermined value so as to alleviate interference from spurious reflections.

Advantageously, plural readings from the counter 92 are averaged to minimize errors but the requirement for this may be alleviated if the resolution of the counter and the frequency of the oscillator 88 is adequate to resolve the required differentiation between various test liquids. The micro-controller 94 resets the pulse counter 92 at the end of each time of flight measurement.

The micro-controller 94 reads the count stored in the counter by way of the analog to digital converter 86 as shown in FIG. 6 and transmits the digitized value to a processor 98 for display or as a signal for some other control function.

Referring now to FIG. 5 temperature measurement is necessary to reliably indicate the possible liquids or proportions of liquid under test as the measured outputs from the refractive index and sonic velocity measurement systems may significantly change in sensitivity, resolution and magnitude over the range of expected operating temperatures. In the case of fuel tested in aircraft wing tanks, the expected operating temperature range may be from $-40°$ C. to $+50°$ C. Preferably the temperature measurement is to an accuracy of about $\pm 1°$ C.

The temperature measurement system as shown in FIG. 5 includes the temperature sensor 56 which is connected with a 5 V power input 75, for example from a battery. The voltage reference 74 is also connected with a 5 V power input 77 and both inputs from the sensor 56 and the voltage reference 74 are supplied to a differential amplifier 79 which emits a signal dependent upon the temperature variation from a predetermined norm to a multiplexer (not shown) connected with the analogue to digital converter 86.

Referring now to FIG. 6, there is shown an overall schematic configuration of the circuitry for an arrangement in which a remote display and interrogator unit such as the unit 98 shown in FIG. 7 is provided to actuate and to receive information from a sensor unit. A refractive index signal conditioning and multiplexing unit 100 comprises the differential amplifier 76, amplifiers 80 and 82 and the multiplexer 84, while a sonic velocity signal conditioning and multiplexing unit comprises the oscillator 88, gate 90, counter 92 and amplifier 96. Both outputs from the units 100 and 102 together with a temperature signal are fed to the analogue to digital converter 86 whose output is passed to the controller 94. The controller 94 also controls the inputs to the units 100 and 102.

In a preferred embodiment, the signal conditioning, multiplexing and analogue to digital conversion could be accomplished, wholly or partly, as an integral part of an application specific integrated circuit including the micro-controller 94 and the voltage reference 74.

Referring to FIGS. 6 and 7, the remote unit 98 is conveniently a small hand-held item which is battery powered and comprises a flash emitter 104, an infra-red transmitter 106 and an infra-red receiver 108. The flash emitter 104 is preferably capable of generating a high speed electronic flash of white light which is initiated by pressing switch means 110. When the flash is directed in the direction of the sensor unit and within the required range, of for example 3 meters, the pulse of light is picked up by a diode 112 powered by a sensor battery 114. The measurement system of the sensor unit is normally cut off from the battery by a switch 116 so is in an inactive mode in order to minimise drainage of the battery 114. However, the flash of light received from the emitter 104 causes a signal to be transmitted by the diode 112 to close the switch 116 and activate the circuitry of the sensor unit.

Conveniently, the switch means 110 comprises a plurality of switches, for example four as shown in FIG. 7, and a coded infra-red signal is emitted by the infra-red emitter 106 shortly after the flash emitter 104 has activated the sensor. The coded signal will depend upon which switch of the switch means 110 is pressed and a sensor unit which does not recognise the coded infra-red signal wil return quickly to its previous inactive mode under the control of the micro-controller 94. This arrangement is useful where a plurality of sensor units, such as the units 10 are disposed close together, for example sensor units in each fuel tank in an aircraft wing, and it is desired to only obtain a read-out from one sensor unit at a time. Each switch in the switch means 110 will be coded for a respective one or more of the sensor units. The coded signal emitted by the infra-red emitter 106 is received by a diode 118 whose output is fed to the micro-controller 94. If the micro-controller recognises the coded signal, the sensor unit remains active and performs the temperature, refractive index and sonic velocity measurements. The measurement data, digitalized in the converter 86 is fed to the micro-controller 94 and transmitted to the infra-red receiver 108 of the remote unit 98 by the infra-red transmitter 120 of the sensor unit. The flash receiver, actuating and communication link circuits of the sensor 10 may also form part of the aforementioned preferred integrated circuit.

The remote unit 98 comprises a micro-computer 122 powered by batteries 124 which are connected by the switch means 110, and is designed to perform the actual decision making tasks given the following essentially raw data: the number of timing pulses related to the time of flight of the sonic velocity pulse(s) (averaged or otherwise), two voltages indicative of the light directed onto the prism and that refracted by the prism, and a voltage representative of the temperature of the sensor unit. The results of the measurement and decision algorithms can be displayed at 126 in any one of a plurality of manners. By way of example quantitative or representative values of refractive index, sonic velocity and temperature may be displayed by the unit 98 or yes/no indications may be given for one or more liquids whose data (i.e. sonic velocity and refractive index over a range of temperatures) has been pre-programmed into the unit. In a preferred embodiment of use of the apparatus with aircraft fuel, the micro-controller 122 may be preset for the specific fuel mixture so that a green light displayed by the display 126 of the remote unit 98 indicates an acceptable fuel while a red light indicates unacceptable fuel. The red light may signify that the sonic velocity and refractive index measurements have determined an incorrect fuel or the correct fuel with a second liquid such as water therein. Further indications may be given by, for example a yellow light indicating no response from the sensor so that the sensor is faulty in some way or did not see the triggering flash while a flashing yellow light may indicate a failure of the remote unit 98.

In the described embodiment, the refractive index sensor may be designed for maximum resolutions for aviation gasolines (i.e. at a refractive index of about 1.4) as the separation between their sonic velocities for different fuel types may be low and even overlap. If the testing apparatus were designed solely for jet fuel application, for example, the refractive index sensor could be optimised to cover the jet fuel refractive index range and increase discrimination confidence between the possible jet fuels. The sensors would still detect an aviation gasoline as a distinctly different class of fuel, particularly by way of the sonic velocity reading. Where the refractive index sensor is set up for maximum resolution with aviation gasolines, the sonic velocity reading may be used as confirmation that there is no other liquid present having a similar refractive index but markedly different sonic velocity, and will be of increased importance in determining fuel type or quality at reduced temperatures. As noted previously sonic velocity measurements may not distinguish between jet fuels and water/ice in the temperature range $-5°$ C. to $+5°$ C., but the refractive index measurements may alleviate difficulties in this range.

The housing 12 conveniently forms part of a fuel tank drain plug and one embodiment is illustrated in FIG. 8 in which the majority of the housing is omitted for convenience. FIG. 8 does show part of the first chamber 18 of the housing as well the drain valve 24d and the through passage 34, but omits the channel 72 for the sensor unit connectors 70.

An aircraft wing 128 has an outer skin 130 with part of the lower portion of the skin being shown in FIG. 8. Within the wing skin, a plurality of fuel tanks are disposed and part of the lower wall 132 of one such tank is shown in the Figure. The lower wall 132 has an opening 134 therethrough which is partly closed by a mounting flange 136 secured to the wall by, for example, screws 138. The flange 136 has a tapered opening 140 therethrough which is co-axial with the opening 134 and is screw threaded. The opening 140 tapers inwardly towards the tank and a tubular adaptor 142 is provided with a correspondingly outwardly threaded tapered plug 144 and an enlarged head 146. The head 146 is internally recessed and the recess 148 is provided with a female screw thread. A tubular spacer 150 has a passage 152 therethrough of the same cross section as a passage 154 through the adaptor and is provided with a small diameter portion 156 which is externally screw threaded to co-operate with the thread of the recess 148. The spacer 150 also has an enlarged head portion 158 having a recess 160 which is internally screw threaded.

The adaptor 142 is provided to fit the appropriate mounting flange 136 while the spacer 150, which screw threadedly co-operates therewith, projects in use through an opening 162 in the lower wing skin 130. The spacer 150 may be omitted if the space between the tank wall 132 and wing skin 130 is reduced, or more, or different spacers may be provided if the space is greater.

The passages 152 and 154 through the spacer and adaptor are sized to closely receive the housing 12 of sensor 10 with the chambers 18 and 20 thereof within the fuel tank. At the outer end of the housing 12 there is provided an outwardly threaded flange 164, which co-operates with the threaded recess 160 in the spacer 150, and a pod 166 extending from the flange outwardly of the wing skin. The internal threads of the recesses 148 and 160 in the adaptor and spacer are the same so if the spacer 150 is omitted the flange 164 of housing 12 may screw directly into the adaptor 142. In use, the adaptor 142 and spacer 150 are threadedly engaged and the housing 12 of sensor 10 is slid through the co-axial passages 152 and 154 until the flange 164 can be threadedly engaged with the recess 160 in spacer 150. The housing 12 is a close sliding fit through the passages 152 and 154 and once it is threadedly engaged with the spacer 150, the assembly of the housing adaptor and spacer may be inserted through the opening 162 in the wing skin 130 and the projecting part of housing 10 and tubular portion 144 of the adaptor inserted through the threaded opening 140 of the mounting flange 136 until screw threaded engagement between the projection 144 and the flange can be made. The assembly is then rotated to cause threaded engagement until the adaptor 142 and flange 136 are tightly engaged. The taper of the opening 140 and tubular portion 144 tends to clamp the housing 12 within the tubular portion and to assist in sealing the assembly. O-rings 168 in the adaptor and the spacer minimize leakage of fuel from the tank along the wall of the housing. The screw threaded engagement between the mounting flange 136 and the adaptor 142 should be such as to minimize the risk of leakage but advantageously a seal 170 is also provided therebetween.

The pod 166 is external to the wing skin 130 and has a stream lined, mushroom shape with an outer seal 172 being provided between the pod and the wing skin. The passage 34 communicating with the drain valve 24 opens through the pod 166 so as to provide access for means introduced through the passage 34 to open the drain valve.

The pod 166 has an annular chamber 174 therein which contains the electronics associated with the refractive index, sonic velocity and temperature measuring systems (not shown in FIG. 8 for convenience) and described with reference to the sensor unit in FIG. 6. The pod and integral housing 10 are conveniently moulded in plastics with the electronics in situ and with the diodes 112, 118 and 120 (also not shown in FIG. 8) for receiving the actuating flash and for receiving and transmitting infra-red signals, respectively, disposed in the outer wall 176 of the pod.

It will thus be appreciated that the sensor 10 and pod 166 may replace a standard drain plug in the bottom of an aircraft fuel tank and permit tests on the liquid as described above. A person standing below the pod 166 may actuate and interrogate the sensor 10 by means of the remote unit 98. If the testing identifies an incorrect fuel, the tank may be readily drained by withdrawing the sensor 10. Alternatively if the tests reveal, for example, water in the correct fuel the water, which tends to sink to the bottom of the fuel tank, may be withdrawn by opening drain valve 24.

FIGS. 9 and 10 identify a minor modification to the housing 12' in which the passage 70 and connectors 72 are replaced by an array 178 of brass pins which extends from connections at 180 with the refractive index, sonic velocity and temperature measuring means to the control electronics which may be disposed in part of the housing such as the pod 166. The array of brass pins is moulded into the housing 12'. Other parts of the housing 12' and components correspond to the housing 12.

FIG. 11 illustrates a modified pod 180, which is shown associated with the housing 12 of sensor 10, and an adaptor 182. The adaptor 182 is of an elongate tubular construction with a reduced cross-section tapered externally threaded portion 184 which is capable of threadedly engaging the opening 140 in the mounting flange 136 to sealingly clamp the housing 12 in the passage 186 of the adaptor 182. The main body portion 188 of the adaptor 182 is of sufficient length to project through the opening 162 in wing skin 130 when the adaptor is threadedly engaged with the mounting flange 136 and has an external screw thread 190. The passage 186 through the adaptor is sized to closely receive the housing 12.

The pod 180 is integral with the housing 12 but has an annular skirt portion 192 coaxial with the housing 12 which projects axially inwardly from the external surface 194 of the pod and is internally screw threaded at 196 to co-operate with the screw thread 190 of adaptor 182. The electronics (not shown) for the sensor unit are housed in an annular chamber 198 of the pod around the skirt 192. The pod 180 as shown has a removable base 200 incorporating an annular seal 202 to co-operate with the wing skin 130. The base 200 is injection moulded in resilient plastics material and snap engages on annular protuberances 204 and 206 on the skirt 192 and at the radially outer edge of the pod respectively. The base 200 may be located on the pod 180 once the electronics have been mounted in chamber 198 and connected with appropriate connectors such as 72 or 178 by way of a passage through the outer surface 194 of the pod.

The pod 180 is similar in other respects to the pod 166 shown in FIG. 8 and is located in a similar manner. Thus, the housing 12 of sensor 10 is slid through the adaptor 182 and the skirt 192 of pod 180 is screw threadedly engaged with the adaptor until the housing 12 projects sufficiently through the portion 184 of the adaptor that the first chamber 18 will be disposed within the tank when the portion 184 is screw threadedly engaged with the opening 140 in mounting flange 136 to sealingly clamp the housing within the adaptor.

Although the housing 12 may only have a length of 72 mm, when the sensor 10 is so disposed in the fuel tank the chamber 20 may be a short distance above the bottom of the tank so may not be able to ascertain the presence of small amounts of water which tend to accumulate at the lowest part. In view of this, it may be desirable for the sensor to be disposed in a well (not shown) of the fuel tank so that the well defines the lowest part of the tank and, for example, the reflector end cap 68 is at the normal lowest level of the tank other than the well.

The sensor 210 shown in FIGS. 12 and 12a is similar to the sensor 10 and comprises the same measuring components, but has a housing 212 formed in two longitudinal halves 214 and 216. The two halves together define the opening 218 to the first chamber 220 in which the refractive index measurement is performed and may be formed in appropriate plastics material which, for example, can be ultrasonically welded together to define the housing. Of minor other difference in this embodiment is that the light path 222 for the light refracted by the prism is foreshortened. Further, an O-ring seal 224 is provided around the prism 36 to alleviate leakage of the liquid under test in chamber 220 behind the prism. It is to be noted that FIG. 12a does not illustrate all of the sensing parts.

FIG. 13 shows a substantially identical arrangement to that in FIG. 12 except that the light path 222' is of similar length to the outgoing light path 226 with the two being divided by a wall 228 and the emitting, receiving and reference diodes 50, 52 and 54 respectively being supported on a printed circuit board 230.

Referring now to FIG. 14, there is shown an embodiment of drain plug 232 for a wing tank which may be associated with testing apparatus such as the sensor 10 except that there is no requirement for the drain valve 24 or for the portion of the housing below the first chamber 18 to be open to atmosphere. Thus, no passage 34 is associated with the pod 232. A tapered adaptor 234 has an external screw thread 236 which co-operates with the thread in opening 140 of mounting flange 136, and a head 238. The adaptor 234 has a passage 240 therethrough in which is received the sensor housing 242 so that the housing projects into the fuel tank in the manner previously described with reference to housing 12. The housing 242 is longitudinally slidable in the passage 240 and is biased upwardly into the tank by a coil spring 244 which is compressed between a flange 246 on the housing 242 and the adjacent end 248 of the adaptor. Maximum insertion of the housing 242 into the fuel tank and through the adaptor 234 is defined by adjustable lock nuts 250 which screw threadedly engage the outer end of the housing. An O-ring seal 252 is provided between the lock nuts and the adaptor head 238.

The housing 242 has an external longitudinal channel 254 formed in the wall thereof which opens into the fuel tank at one end and extends in the closed position shown to an O-ring seal 256 in the passage 240 of the adaptor.

When it is desired to drain a small amount of fuel from the tank, the pod 232 and housing 242 are manually withdrawn away from the wing and tank against the bias of spring 244 whereby the channel 254 extends below the level of O-ring seal 256. The spring 244 will return the assembly of pod and housing to the closed position when the pod is released.

The pod 232 has an internal chamber 258 in which the electronics (not shown) for the sensors of housing 242 are located and with appropriate receivers disposed in the external wall of the pod as described with reference to FIG. 6. The pod may be moulded around the electronics components integrally with or separately from the housing 242 and has a flexible sealing edge 260 which in the closed position engages the wing skin 130. The sealing edge 260 forms a basin 262 with the base 264 of the pod which will tend to collect the fuel drained through the channel 254 when the channel is opened, and a drain hole 266 is provided in the sealing edge to allow controlled drainage of this fuel.

FIG. 15 illustrates in enlarged scale a modification of part of the housing 12 of FIG. 1 In which the reference photodiode 54 the temperature sensor 56 and the sonic velocity transmitter 60 are all potted in thermosetting resin 268 so as to locate these components and a printed circuit board 270 supporting the diodes 50 and 52 and to seal the potted components from the liquids under test.

In FIG. 16, the components in the housing 272 are the same as in the housing 12 of FIG. 1 but they are arranged in an inner casing 274 of appropriate plastics material. The various components of the testing apparatus may be pre-disposed in the inner casing which may then be bonded by, for example, appropriate glue or by ultrasonic welding to the housing 272. A channel 276 may be formed in the inner surface of the housing 272 and the connectors fed from the electrical components of the testing apparatus through a hole 278 in the inner case into the channel 276 which extends to the microcontroller or other appropriate control means.

The wall 44' extends the full length of the chamber 42' between the prism 36 and the sonic velocity transducer 60, and as in the embodiment of FIG. 12 the light path 280 for the refracted light to the receiving photodiode 52 is foreshortened compared to the light path between the diode 50 and the prism. The reference diode 54 and the temperature transducer 56 as well as the sonic velocity transducer 60 are potted in resin 282 so as to seal the chamber 42'. The transducer face 62 is free of resin in chamber 20.

Referring now to FIG. 17, there is shown schematically an integral hand-held liquid tester and display unit 300. The unit 300 has a handle 302 and a test head 304. The test head 304 comprises a single chamber 306 which is sealed except for a part annular opening 308 in a cover 310. The cover 310 is screw threadedly engaged with the chamber wall so that it may be removed to facilitate cleaning of the chamber 306. The opening 308 is in a recessed portion 312 of the cover 310 from which projects a central probe 314 which may, for example, be introduced into the drain outlet of a drain plug to displace the valve into an open position following which fuel flows down the exterior of the probe into the recess 312 and from there into the chamber 306 through the opening 308. The body of the chamber 306 comprises transparent material 316 so that it may be visually ascertained when the chamber is full.

A prism 318 is supported on the base 320 of the chamber 306 with a multifaceted end 322 in the chamber. The emitter, receiver and reference diodes associated with the prism 318 for measuring the refractive index of liquid in the chamber 306 in the manner described with reference to FIG. 3 are schematically represented by the one diode means 324 and are connected by connectors 326 to a printed circuit board 328 in the handle 302.

A sonic velocity transducer 330 is also supported in the base 302. The piezo-electric cell 330 is connected to the printed circuit board 328 by connector 332 and transmits a sonic pulse to a reflector 334 spaced from the cell 330 in the longitudinal direction of the pulse by a frame 336 having a plurality of slots 338 therethrough to permit access of the test liquid in the chamber 306. The cell 330 also acts as the pulse receiver and transmits a signal to the printed circuit board 328. The sonic velocity measurement is performed in the manner described with reference to FIG. 4.

The unit 300 is powered by batteries 340 disposed in the handle 302 and electronics similar to those described with FIG. 6 incorporated in the printed circuit board 328 are activated by the test button 342. The major difference over the circuitry shown in FIG. 6 is that the sensor unit and read-out unit are integrated so that the activating unit 104/112 and infra-red transmitters and receivers are unnecessary. In their place, the printed circuit board may incorporate the display unit 126 of FIG. 6 which is visible through a lens 344 in the handle 302. As before, the display unit may take any appropriate form.

Although not shown in FIG. 17, a temperature sensor would be a necessary feature of the unit 300 so that the processor could account for variation in refractive index and sonic velocity due to temperature changes.

FIG. 18 illustrates schematically liquid testing apparatus 400 which may be used for determining the proportion of alcohol in, for example, a methanol/unleaded petrol fuel mixture for a flexible fuelled vehicle. The apparatus 400 comprises a housing 402 which is disposed in the fuel line 404 between the mixed fuel tank and the engine. The fuels are mixed and flow continuously through the housing 402 by way of the fuel line 404 during use of the engine and the apparatus 400 emits a signal at 406 which is indicative of the alcohol content in the fuel which may be passed to the engine management system (not shown) with other appropriate signals to ensure optimum running of the engine. A voltage signal at 406 varies linearly according to the methanol content of the fuel for example from 12 volts at 100% methanol to 3 volts at 100% unleaded petrol.

Since space in the housing 402 is not at a premium as in the sensor 10, it is not necessary for the refractive index probe and sonic velocity probe to be coaxially aligned, but in all other respects the parts of the apparatus 400 are substantially the same as the sensor 10 with appropriate modifications being apparent to those skilled in the art.

Thus, the apparatus 400 comprises a prism 36, a sonic velocity chamber 20 and a temperature sensor 56 all of which are supported on a removable cap 408 of the housing 402 and connected to a micro-controller 94. The cap 408 is removable so as to permit cleaning and other access to the apparatus.

Clearly, the prism 36 will have associated with it the previously described photodiodes and other parts which are not shown and will not be described further. Likewise, the sonic velocity chamber 20 will have associated with it a piezo-electric cell and reflecting surface as previously described.

The circuitry for the apparatus 400 is identical to that described with reference to FIGS. 3 to 6, except that with reference to FIG. 6 the flash emitters 104, 106 and 108 and the receivers 112, 118 and 120 being replaced by direct connections between the micro-controllers 94 and 98 and, accordingly, the battery 114 and switch 116 being omitted entirely. Additionally, the display unit 126 is replaced by the aforementioned engine management system into which other signals relevant to the optimum running of the engine may be introduced.

Alternatively, a display unit (not shown) may also be provided to indicate the proportions of the measured fuel.

It will be readily understood that the described embodiments are given by way of example only and that many modifications and variations may be made thereto. All such modifications and variations should be considered as within the scope of the present invention.

We claim:

1. Liquid testing apparatus including a housing comprising means defining at least one chamber capable of receiving liquid to be tested, optically transparent reflecting means in the housing and having a plurality of reflecting surfaces in said means defining at least one chamber, light transmitting means in the housing for radiating light onto said reflecting means, reflected light receiving means in the housing for receiving light from the transmitting means which has been reflected on said plurality of surfaces and means for converting said reflected light into a first electrical signal indicative of the refractive index of the liquid, means in the housing for generating at least one sonic pulse and for transmitting same through liquid to be tested in said means defining at least one chamber, means in the housing for generating a second electrical signal indicative of the sonic velocity of the liquid and derived from said at least one transmitted pulse, means in the housing for sensing the temperature of the liquid under test, means in the housing for generating a third signal dependent on the temperature sensed and means for transmitting said first, second and third signals for determining the quality of the tested liquid.

2. Liquid testing apparatus as claimed in claim 1 and incorporating an engine control device, said first and second signals or said at least one further signal being capable of being transmitted to the engine control device to modify the running of the engine.

3. Liquid testing apparatus as claimed in claim 1 and comprising indicating means to indicate the quality of the tested liquid.

4. Liquid testing apparatus as claimed in claim 3 wherein the indicating means is remote.

5. Liquid testing apparatus as claimed in claim 4 wherein the remote indicating means is cordless.

6. Liquid testing apparatus as claimed in claim 5 which is normally dormant and is actuated by a trigger signal and wherein the remote indicating means has means for transmitting the trigger signal.

7. Liquid testing apparatus as claimed in claim 6 wherein the remote indicating means has means for also transmitting a coded signal whereby the apparatus only remains actuated to perform the tests if the correct coded signal is transmitted.

8. Liquid testing apparatus as claimed in claim 3 which comprises a single housing incorporating the indicating means.

9. Liquid testing apparatus as claimed in claim 1 which is normally dormant and is actuatable by a trigger signal.

10. Liquid testing apparatus as claimed in claim 1 wherein there is one said chamber capable of receiving liquid to be tested and the optically transparant reflecting means and the sonic pulse generating and transmitting means open to said chamber in side-by-side manner.

11. Liquid testing apparatus as claimed in claim 1 wherein the optically transparent reflecting means and the sonic pulse generating and transmitting means are open to respective chambers with said optically transparent reflecting means and the sonic pulse generating and transmitting means being disposed between said chambers.

12. Liquid testing apparatus as claimed in claim 11 wherein the optically transparent reflecting means, the sonic pulse generating and transmitting means and said respective chambers are disposed in an elongate sensor housing having slotted walls for access of the liquid under test to the chambers.

13. Liquid testing apparatus as claimed in claim 1 which is incorporated in a container drain plug.

14. Liquid testing apparatus as claimed in claim 13 in which the drain plug comprises a drain valve for withdrawing the liquid under test from the chamber or from at least one of the chambers.

15. Liquid testing apparatus as claimed in claim 1 which comprises means for at least partly collimating the light transmitting means.

16. Liquid testing apparatus as claimed in claim 1 which comprises means for averaging a multitude of the sonic pulses.

17. Liquid testing apparatus as claimed in claim 1 in which the plurality of reflecting surfaces of the reflecting means is in the form of a continuously curved reflecting surface.

* * * * *